(12) United States Patent
Petersen et al.

(10) Patent No.: US 7,694,682 B2
(45) Date of Patent: Apr. 13, 2010

(54) LARYNGEAL MASK AND A METHOD MANUFACTURING SAME

(75) Inventors: Lasse Petersen, Vedbæk (DK); Peer Hoffmann, Stenløse (DK)

(73) Assignee: AMBU A/S, Ballerup (DK)

( * ) Notice: Subject to any disclaimer, the term of this patent is extended or adjusted under 35 U.S.C. 154(b) by 615 days.

(21) Appl. No.: 10/552,160

(22) PCT Filed: Apr. 7, 2004

(86) PCT No.: PCT/DK2004/000260

§ 371 (c)(1),
(2), (4) Date: Nov. 16, 2005

(87) PCT Pub. No.: WO2004/089453

PCT Pub. Date: Oct. 21, 2004

(65) Prior Publication Data

US 2006/0201516 A1  Sep. 14, 2006

(30) Foreign Application Priority Data

Apr. 11, 2003 (DK) ............... 2003 00563
May 22, 2003 (DK) ............... 2003 00769

(51) Int. Cl.
*A61M 16/00* (2006.01)
*A61M 16/04* (2006.01)
*A61M 16/08* (2006.01)

(52) U.S. Cl. ............... 128/207.15; 128/207.14; 128/200.26; 128/207.16; 128/200.24; 604/96.01; 604/174

(58) Field of Classification Search ............ 128/200.26, 128/200.24, 207.14, 207.15, 207.16
See application file for complete search history.

(56) References Cited

U.S. PATENT DOCUMENTS

| 5,241,956 | A | * | 9/1993 | Brain | 128/207.15 |
| 5,305,743 | A | * | 4/1994 | Brain | 128/207.15 |
| 5,391,248 | A | * | 2/1995 | Brain | 156/242 |
| 6,422,239 | B1 | | 7/2002 | Cook | |
| 6,439,232 | B1 | | 8/2002 | Brain | |
| 6,604,525 | B2 | * | 8/2003 | Pagan | 128/207.15 |
| 6,705,318 | B1 | * | 3/2004 | Brain | 128/207.14 |

(Continued)

FOREIGN PATENT DOCUMENTS

EP  0 842 672  5/1998

(Continued)

*Primary Examiner*—Steven O Douglas
*Assistant Examiner*—Clinton Ostrup
(74) *Attorney, Agent, or Firm*—Dykema Gossett PLLC

(57) ABSTRACT

The invention relates to a laryngeal mask (1) comprising at least one airway tube (2) and a mask portion (3), which mask portion (3) comprises a top face (4) and a bottom face (5), said bottom face (5) comprising a lumen (6) that communicates with the tube (2) interior (7), and said top face (4) comprising a closed transition face (8), and said mask portion (3) being at least on the bottom face in the periphery delimited by an inflatable cuff (9), and said mask portion (3) comprising a joint throughout the entire internal circumference of the cuff (9), facing towards the lumen (6) and for providing a closed cuff. Hereby a product is provided which is formed integrally with regard to mask portion and airway tube portion thereby eliminating the risk that the two parts are separated in use.

10 Claims, 16 Drawing Sheets

U.S. PATENT DOCUMENTS

| | | | | |
|---|---|---|---|---|
| 2002/0020416 | A1* | 2/2002 | Namey | 128/205.25 |
| 2002/0078961 | A1* | 6/2002 | Collins | 128/207.15 |
| 2002/0112728 | A1 | 8/2002 | Landuyt | |
| 2003/0037790 | A1 | 2/2003 | Brain | |

FOREIGN PATENT DOCUMENTS

| | | | |
|---|---|---|---|
| EP | 1 219 316 | | 7/2002 |
| GB | 2367525 A | * | 4/2002 |
| WO | WO94/17848 | | 8/1994 |

\* cited by examiner

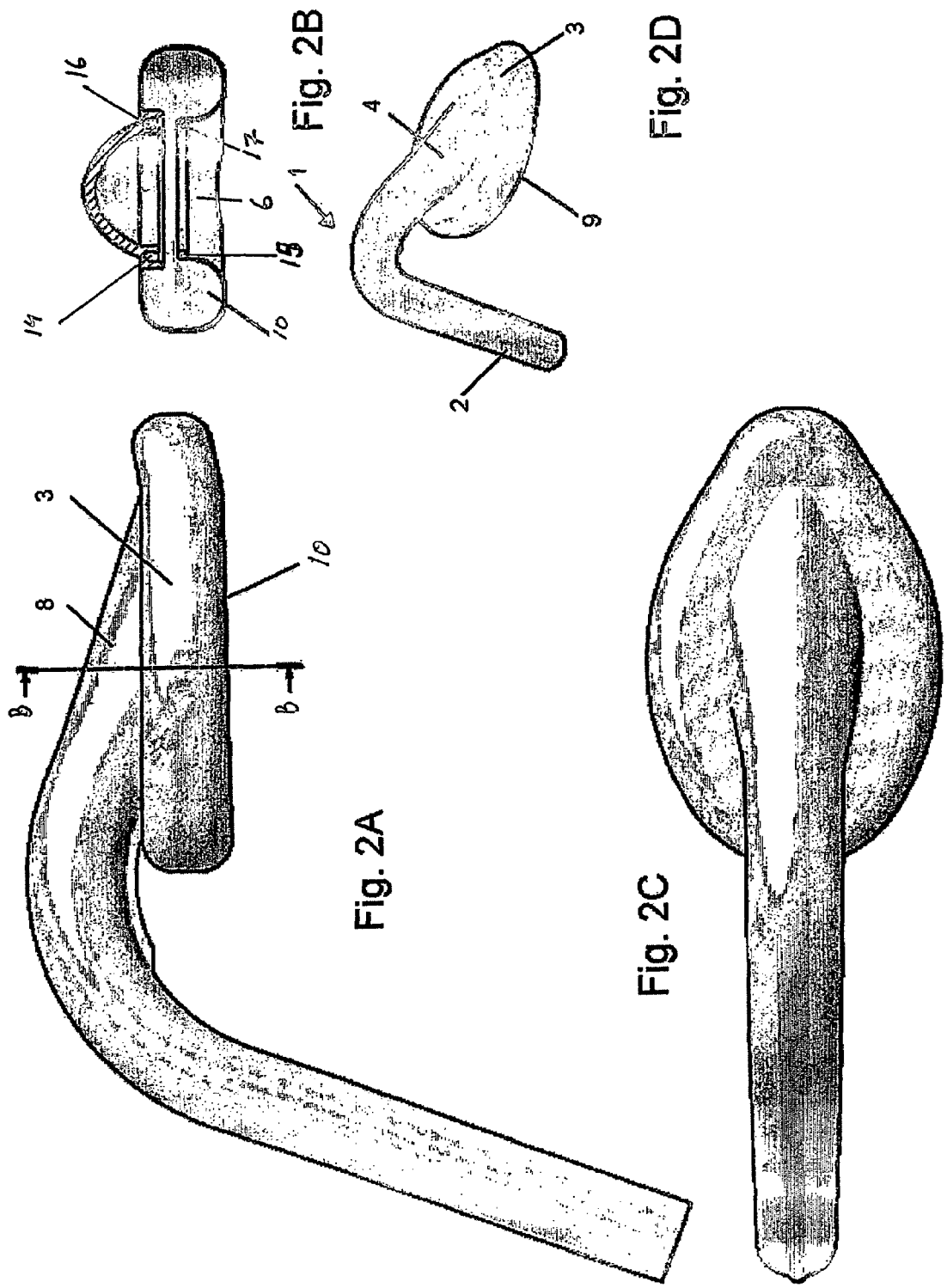

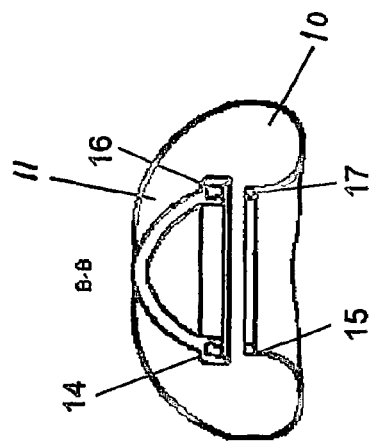
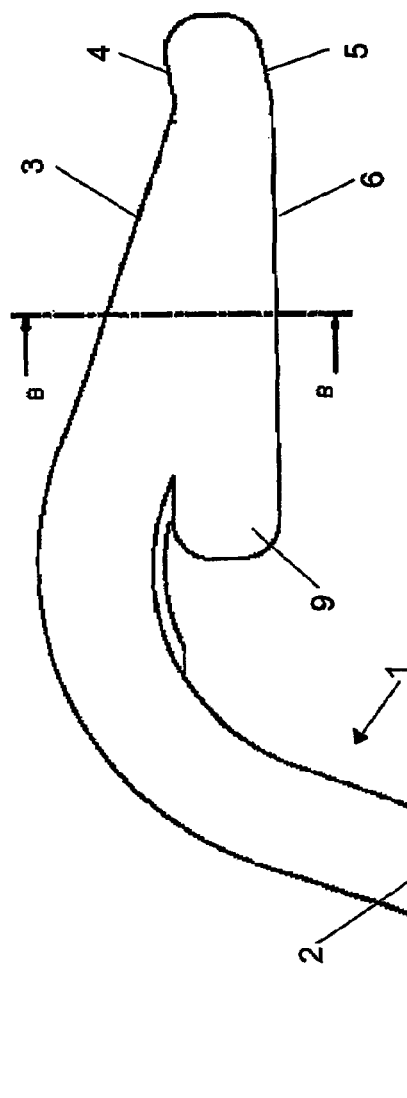
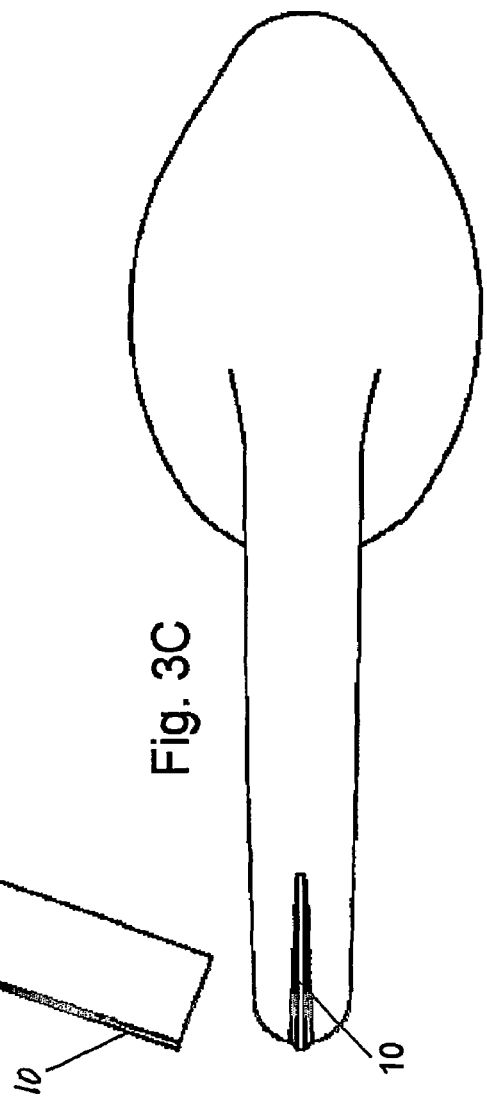

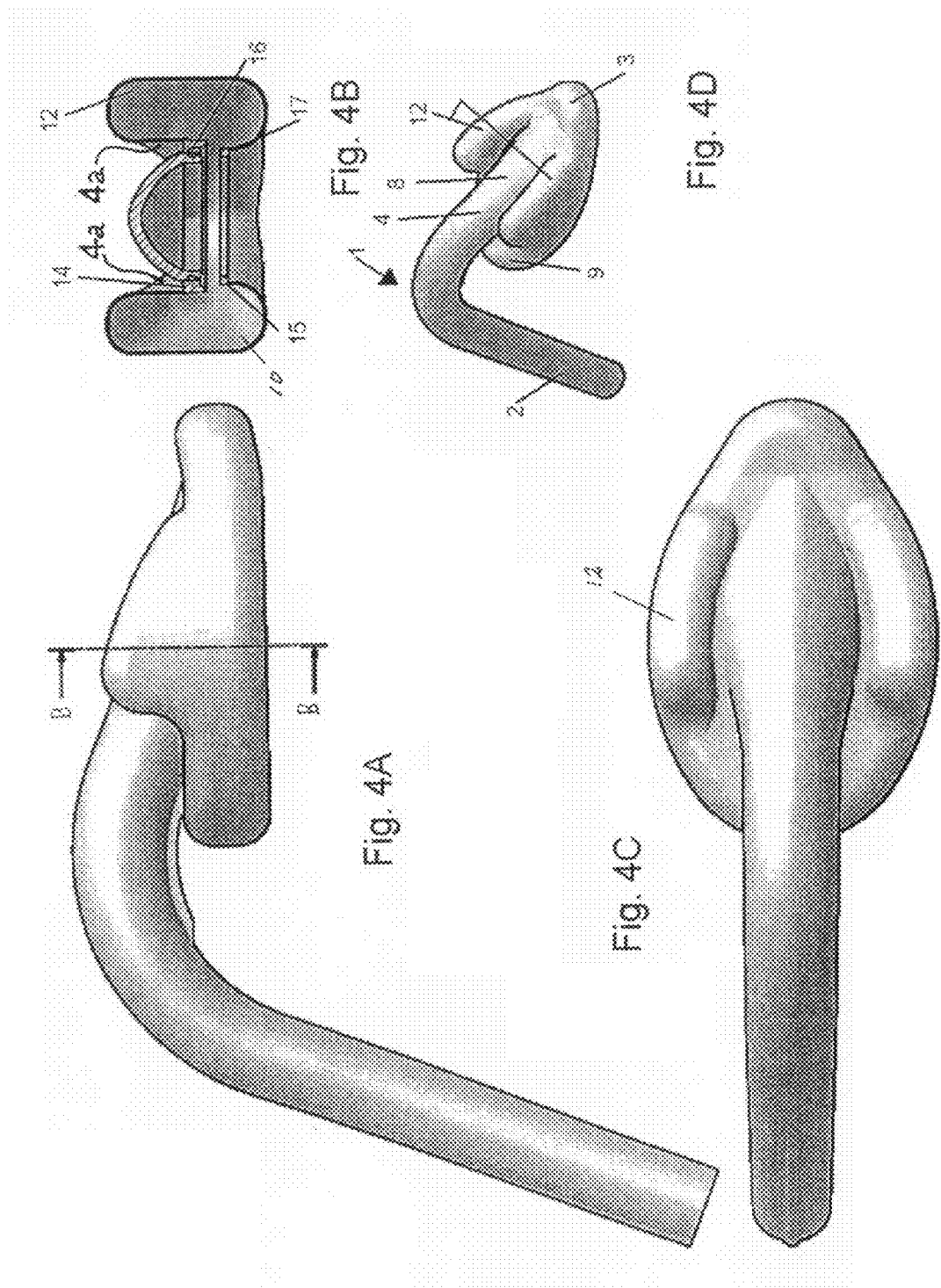

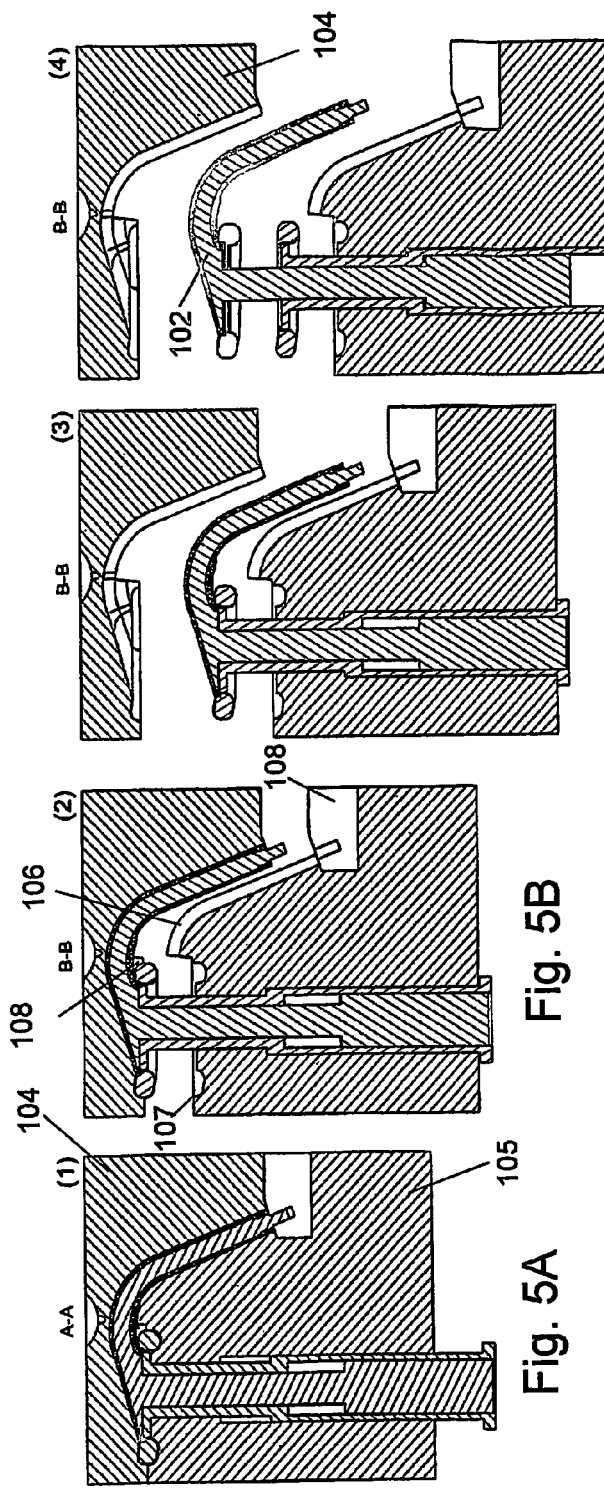

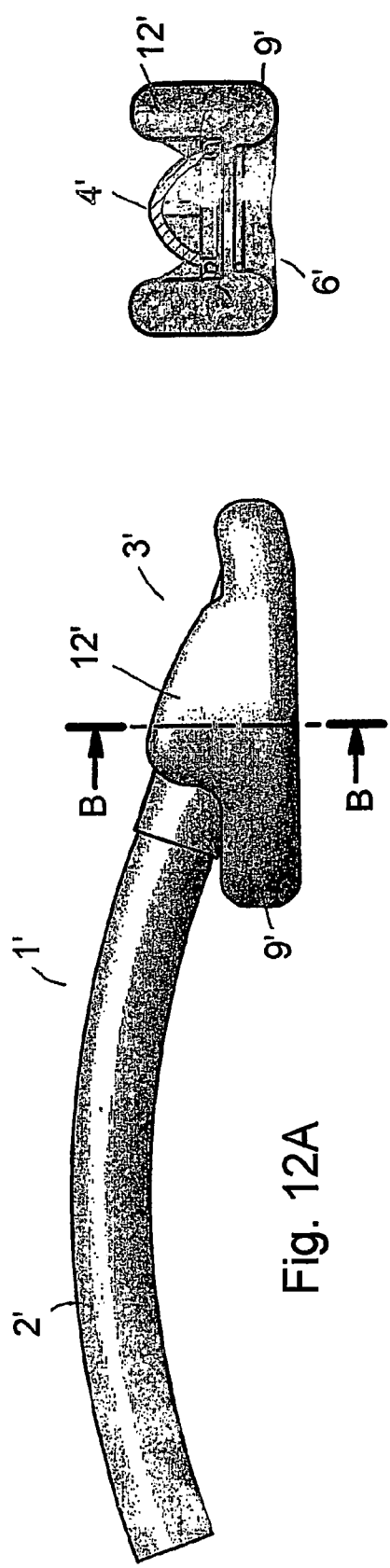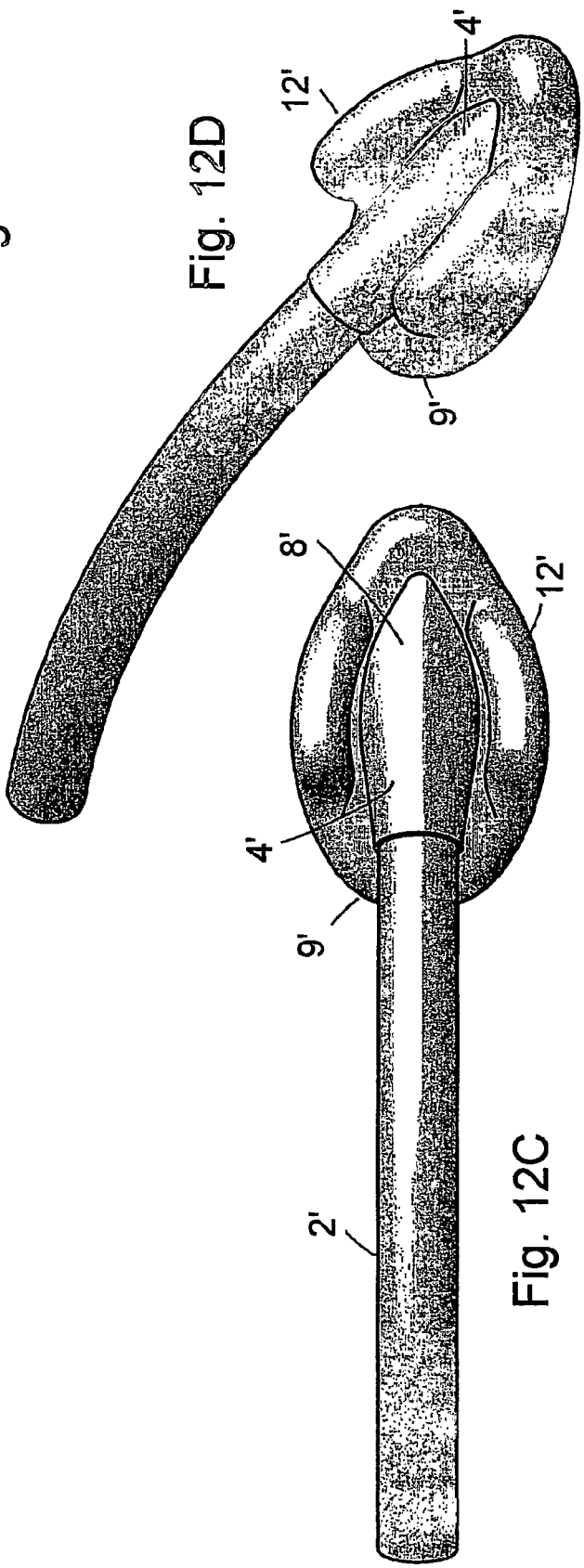

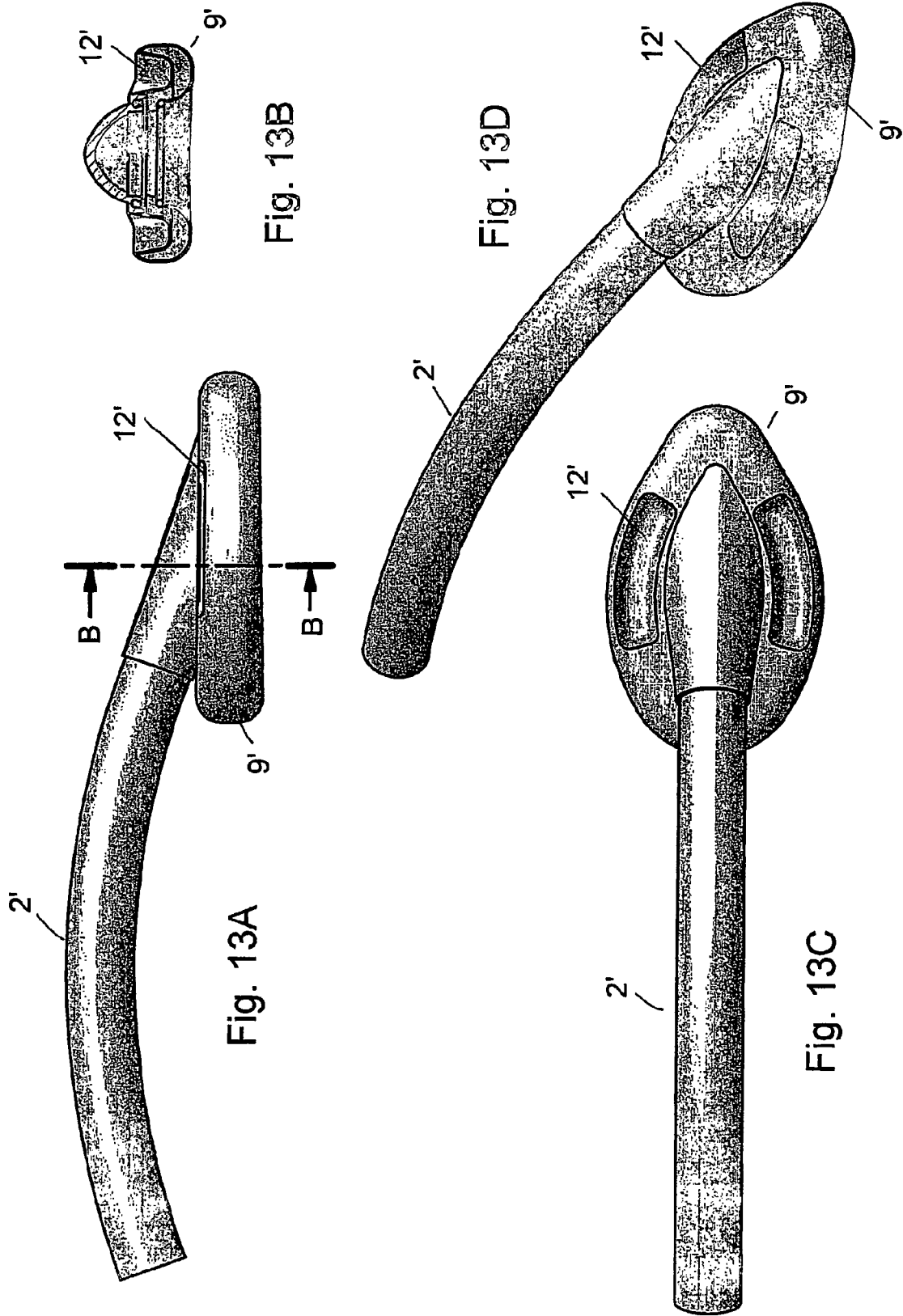

LARYNGEAL MASK AND A METHOD MANUFACTURING SAME

BACKGROUND OF THE INVENTION

1. Field of the Invention

The invention relates to a laryngeal mask that includes at least one airway tube and a mask portion, the mask portion including a top face and a bottom face, the bottom face including a lumen that communicates with the tube interior, and the top face including a closed transition face; and wherein the mask portion is delimited in its periphery by an inflatable cuff at least on the bottom face. The invention also relates to a method of manufacturing such a laryngeal mask.

2. The Prior Art

EP-1 259 595 discloses the manufacture of laryngeal masks by means of rotational moulding, and wherein exclusively the mask portion as such is manufactured in that process.

From EP-9 35 971 and EP 922 465 it is known to manufacture the mask portion by blow moulding.

Laryngeal masks are used in connection with the establishment of passage of air to the respiratory tracts, while simultaneously the air passage to the oesophagus is blocked. The laryngeal mask is shaped such that its lumen within the mask portion as such faces towards the laryngeal opening, and wherein there is provided an inflatable elliptical cuff around that lumen that forms a seal around the laryngeal opening. To the cuff there is a tubular connection that is connected to a balloon part and a valve, and by which the peripheral cuff of the mask is inflated thereby ensuring a tight abutment of the product; likewise it is possible to perform a deflation of the peripheral cuff by extraction of air via said valve.

However, the prior art laryngeal masks are all manufactured as multi-component products, air tube and mask portion not being manufactured integrally but rather as two separate components that are subsequently to be assembled. Likewise it is known that the mask portion as such is manufactured as two components; viz as a cuff portion and a connecting element (mount member) that are subsequently to be connected to each other. On the one hand, such additional assembly process is costly and, on the other, there is also a risk that the laryngeal mask separates at the assembly part as such, which may have serious consequences to the patient in connection with anaesthesia, etc.

It is thus the object of the present invention to provide, on the one hand, a laryngeal mask and a method that remedy the above-referenced problems and whereby it is possible to provide a product that is configured in one piece with respect to mask portion and at least a part of the airway tube portion, thereby eliminating the risk of the two parts separating in use, and wherein the material thickness of the laryngeal mask varies and can be regulated unequivocally by the process. Hereby the requisite mechanical and elastic properties are imparted to the laryngeal mask in selected and well-defined areas.

SUMMARY OF THE INVENTION

This object is accomplished by a laryngeal mask of the kind described above and wherein, additionally, at least a part of the airway tube and the mask portion are formed integrally with each other for providing an assembled integral structure and without assembly components between airway tube and mask portion; and wherein the mask portion comprises a joint throughout the entire inner circumference of the cuff and facing towards the lumen and for providing a closed cuff.

The object is also accomplished by a method of the kind described in the introductory part, and wherein the process comprises injection moulding of a laryngeal mask in a closed mould part, said laryngeal mask comprising at least a part of the airway tube portion and the mask portion, and wherein the laryngeal mask is discharged from the mould, the peripheral cuff of the laryngeal mask comprising an annularly extending opening therein pointing towards the lumen and being delimited by an upper peripheral edge and a lower peripheral edge.

Thus the laryngeal mask is manufactured in a closed mould, wherein a suitable elastic polymer material, eg silicon rubber, PVC, TPE (thermoplastic elastomer) (eg SEBS), is injected while highly pressurized, eg at an initial pressure of about 55 MPa (when the material used is SEBS) and at a temperature of 210° C. of the material SEBS, and at a temperature of 50° C. of the closed mould that consists of two mould parts that can be moved away from each other. Perpendicular to the direction of movement of these mould parts, two lateral pull parts are also provided that are subsequently activated.

The process parameters as such are a function of the selected material, SEBS being merely exemplary of such.

Moreover the mould comprises at least one core for providing the interior cavity in cuff and airway tube portion.

Following injection of the plastics material, the laryngeal mask must subsequently be ejected from the mould which takes place by the two mould parts being moved away in relation to each other and subsequently by the lateral pulls being moved perpendicular to the direction of movement thereof, whereby the laryngeal mask as such is now caused to adhere to the one half part of the first mould part. Subsequently the core is pulled away in the same direction of movement as that of the movable first part, and now the laryngeal mask is fixed on the core part. The core can now be removed, albeit the peripheral cuff encloses a core part corresponding thereto, since the elastic polymer of the peripheral cuff ensures precisely via an annularly extending opening that it is possible to withdraw the core.

The laryngeal mask is ejected from the mould for instance by pressurized air being blown in between core and the surrounding plastics material. Now a product is provided comprising mask portion and airway tube portion, and wherein the peripheral cuff has an annularly extending opening that faces towards the lumen that constitutes the lower part of the mask and communicates with the tube interior, said annularly extending opening having a distance between its upper peripheral edge and its lower peripheral edge of 1-8 mm. The upper and lower peripheral edges are shaped as a tongue and groove arrangement, respectively, and wherein it is possible to subsequently arrange the product in a holder, apply a string of glue to the groove part and press the tongue there into, whereby a sealing of the peripheral cuff is accomplished, thereby transforming the cuff to a closed annularly extending cavity.

It is noted that the joint between the upper and the lower peripheral edge, also designated edge delimitation, can be configured in other ways than indicated above. For instance, the lower face may assume a well-defined, annular, flat face that is suitable for receiving the lower edge delimitation; and wherein that edge delimitation may be configured eg with a wide face edge that can be fixed to the opposite face eg. by a welding or a gluing. It is also noted in this context that the inner circumference is to be understood as the part of the cuff that is situated on the bottom face and points in a direction towards the lumen. The cuff may extend to the top face of the mask portion such that the top face also comprises a cuff.

By the above-referenced procedure a product is provided that possesses the mentioned properties and wherein a stud is subsequently formed on the peripheral cuff by integral moulding and in connection with the moulding process a thin tube is fixedly mounted and is in communication with a valve and a balloon. Through this an adjustment of the volume of the cuff is performed, as it is possible to press in air through the thin tube—and likewise it is possible to draw out air.

The laryngeal mask functions in that, prior to insertion into the patient, the eg elliptical cuff is non-inflated, ie collapsed, and subsequently, when it has achieved its correct abutment around the laryngeal opening, inflation thereof is performed for bringing about a tight connection. As a minimum the cuff is provided on the bottom face of the mask and, as mentioned above, it may optionally be provided with a cuff on the top face which is coherent with the lower one.

By provision of a laryngeal mask according to the invention, it is accomplished that varyingly flexible and rigid properties are imparted to the laryngeal mask in selected sections thereof in response to which mechanical properties are desired. Thus, it is desirable that the cuff is very flexible, and likewise it is desirable that any portions or sections of the cuff can be inflated more than other portions, which is accomplished in that portions of the cuff have a thinner wall thickness than the surrounding sections, while it is desirable that that the airway tube as such is more rigid in order for it not to kink, and therefore the airway tube can be configured with a generally greater material thickness. The term inflatable portion is intended to designate those portions that are, during inflation, stretched due to their poor thickness relative to the surrounding sections.

By providing a laryngeal mask according to the invention, convenient outer shapes of the cuff are accomplished with respect to that part of cuff that faces in the same direction as the lumen as well as the part that is optionally situated on top of the top face.

By providing a laryngeal mask according to the invention, a smooth transition between, respectively, the thickness of the airway tube and the wall thickness of the cuff as such is accomplished. Thus, the top face will at all times have a wall thickness larger than the wall thickness of the inflatable cuff and preferably, but not necessarily, it will have a wall thickness smaller than that the airway tube.

By providing a laryngeal mask according to the invention, a number of properties are accomplished for the cuff, as mentioned above, including bulging of portions of the cuff that will expand more than the rest when, in use, the cuff is inflated.

By providing a laryngeal mask according to the invention, it is accomplished that the part of the airway passage that is situated opposite the mask portion and is in contact with the teeth of the patient in use is so rigid that there is not risk of the airway tube being bitten apart during use of laryngeal mask and likewise the risk of the tube kinking is eliminated. The rigid tubing can be manufactured from a convenient plastics material, e.g., rigid PVC, and likewise it can be manufactured from a convenient metal alloy; e.g., steel. However, it is preferably manufactured from the same material as the remainder of the laryngeal mask. The rigid tubing may extend all the way from the location on the airway tube where a connecting part (connector) for providing a connection between an air source is usually arranged and to the location on the airway tube, where the mask portion as such commences i.e., the rigid tubing may have both a straight course and a curved section. It is noted that conveniently the rigid tubing will have a conical connector at the end that is intended to face away from the patient in use, said connector establishing communication with a respiratory apparatus or an anaesthetic inspiration circuit.

By providing a laryngeal mask according to the invention, it is accomplished that increased flexibility is imparted to the rigid tubing, whereby the tubing and the airway tube can be bent without kinking, however. For instances the grooves may be ribbed or they may be configured as threading.

By providing a laryngeal mask according to the invention, it is accomplished that parts of the airway tube as such become so rigid that the risk of it kinking in use is reduced, while yet it remains bendable. The ribs may be used for an embodiment of the invention in which a rigid tubing is not used in the airway tube, or they can be used in parts of the airway tube that are not provided with a rigid tubing as taught above.

Further details regarding the laryngeal mask are as taught in the following:

The laryngeal mask may well be provided with a lubricant or cream or antibacterial agent, at least on the mask portion as such, whereby the laryngeal mask is more easily arranged in the pharynx of the patient.

Moreover an additional inflatable bellows shaped as an enlargement of the cuff may be arranged in the area of the cuff's longitudinal axis, ie essentially corresponding to the area where the airway tube is connected to the mask, and whereby a rather more voluminous cuff is accomplished that will per se also enable improved abutment on the rear part of the pharynx.

Moreover the product may comprise two inflatable lateral bellows that are arranged on the top face of the mask in parallel with the major axis of the elliptical cuff/the longitudinal axis of the cuff, and whereby improved sealing is accomplished of the connection between the lumen of the laryngeal mask and the laryngeal opening. Thereby a set of passages are provided between the lateral bellows and the top face of the mask portion that allow vomit, if any, to pass without the laryngeal mask being displaced in a direction away from the laryngeal opening.

The invention also relates to a method of manufacturing a laryngeal mask.

BRIEF DESCRIPTION OF THE DRAWINGS

The invention will now be explained with reference to the drawing, in which:

FIGS. 1A-D teach a laryngeal mask in a perspective view, and wherein FIGS. 1A-C show the laryngeal mask to which both a valve and a balloon are connected, and wherein a connector is mounted at the free end of the airway tube;

FIGS. 2A-D show a first exemplary embodiment of a laryngeal mask according to the invention, wherein Figure A is a side view, Figure B is a sectional view along the line B-B, FIG. 2C is a top view of the product, and finally Figure D is a perspective view;

FIGS. 3A-C show an alternative exemplary embodiment of a laryngeal mask, comprising a side view A—a sectional view B along the line B-B and seen from above C;

FIGS. 4A-D show a third exemplary embodiment of the laryngeal mask, wherein the drawings correspond essentially to those shown in FIG. 3, but wherein a perspective view of the finished product is also shown in FIG. 4D;

FIG. 5 shows a mould part and its movement pattern during manufacture of a laryngeal mask according to the invention;

FIGS. 12A-D show a multi-component laryngeal mask, wherein Figure A is a lateral view, Figure B is a sectional view along the line B-B, Figure C is a top view of the product, and finally Figure D is a perspective view; and FIGS. 13A-D show an embodiment of a multi-component laryngeal mask shown in FIG. 12, wherein Figure A is a lateral view, Figure B is a sectional view along the line B-B, Figure C is a top view of the product, and finally Figure D is a perspective view.

DETAILED DESCRIPTION OF THE PREFERRED EMBODIMENTS

Figure 1A:
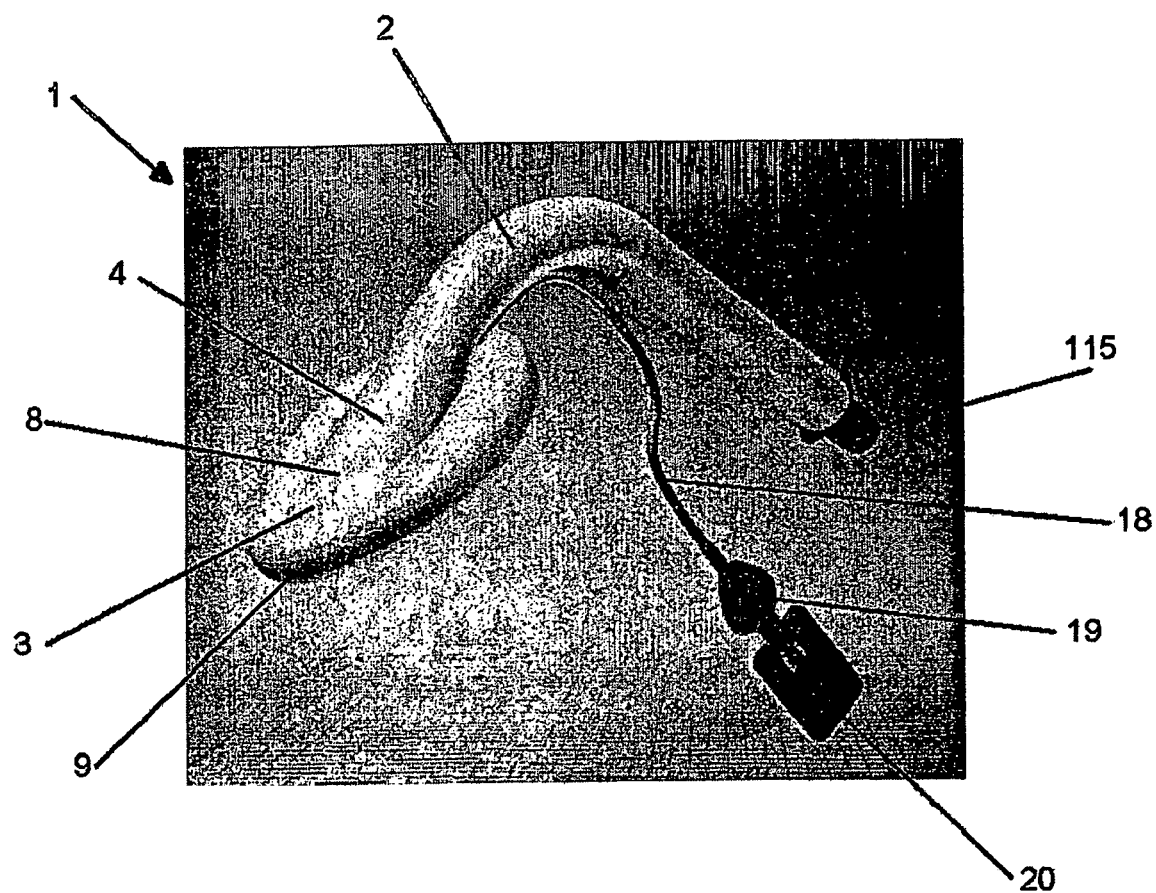

FIGS. 1A-d show an exemplary embodiment of a laryngeal mask 1 comprising at least one airway tube 2 having a circular cross section and a mask portion 3, said mask portion 3 comprising a top face 4 and a bottom face 5. The bottom face 5 comprises a lumen 6 that communicates with the tube 2 interior 7. The top face 4 comprises a closed, preferably smooth transition face 8. This face 8 is preferably convex and it may also comprise reinforcing ribs on its outer or inner face. The mask portion 3 is delimited at the periphery by an inflatable cuff 9. Its outer contours may be drop-shaped, elliptical, oval, etc. The airway tube 2 and the mask portion 3 are formed integrally within each other for providing an assembled integrated product without connecting elements between the airway tube 2 and mask portion 3.

The manufacture of the laryngeal mask takes place by an injection moulding process and the laryngeal mask is manufactured from a polymeric material. The peripheral cuff 9 is provided with a stud 21 that is connected to a further tube 18 which is thin compared to the airway tube 2 and having at its free end mounted a valve 20 and a balloon 19. Through this inflation and deflation of the peripheral cuff 9 is performed in accordance with known principles. The second tube 18 may conveniently be secured to the outer face of the airway tube 2 along same, at least in as much as the first 1-5 cm from the stud 21 is/are concerned. This may be accomplished eg by the airway tube 2 being equipped with a recess or longitudinally extending ribs (not shown) into which the second tube 18 can be pressed and optionally adhered to.

FIGS. 1A-D show the laryngeal mask in its inflated state, wherein the peripheral cuff 9 would be collapsed if it had been depleted of air via the valve 20.

FIG. 1A shows the case in which, at its free end—ie opposite the end where the mask portion 3 is located—a conical connector 115 is mounted on the airway tube 2, which connector 115 establishes connection to a respiratory apparatus or an anaesthetic system.

Figure 1B:
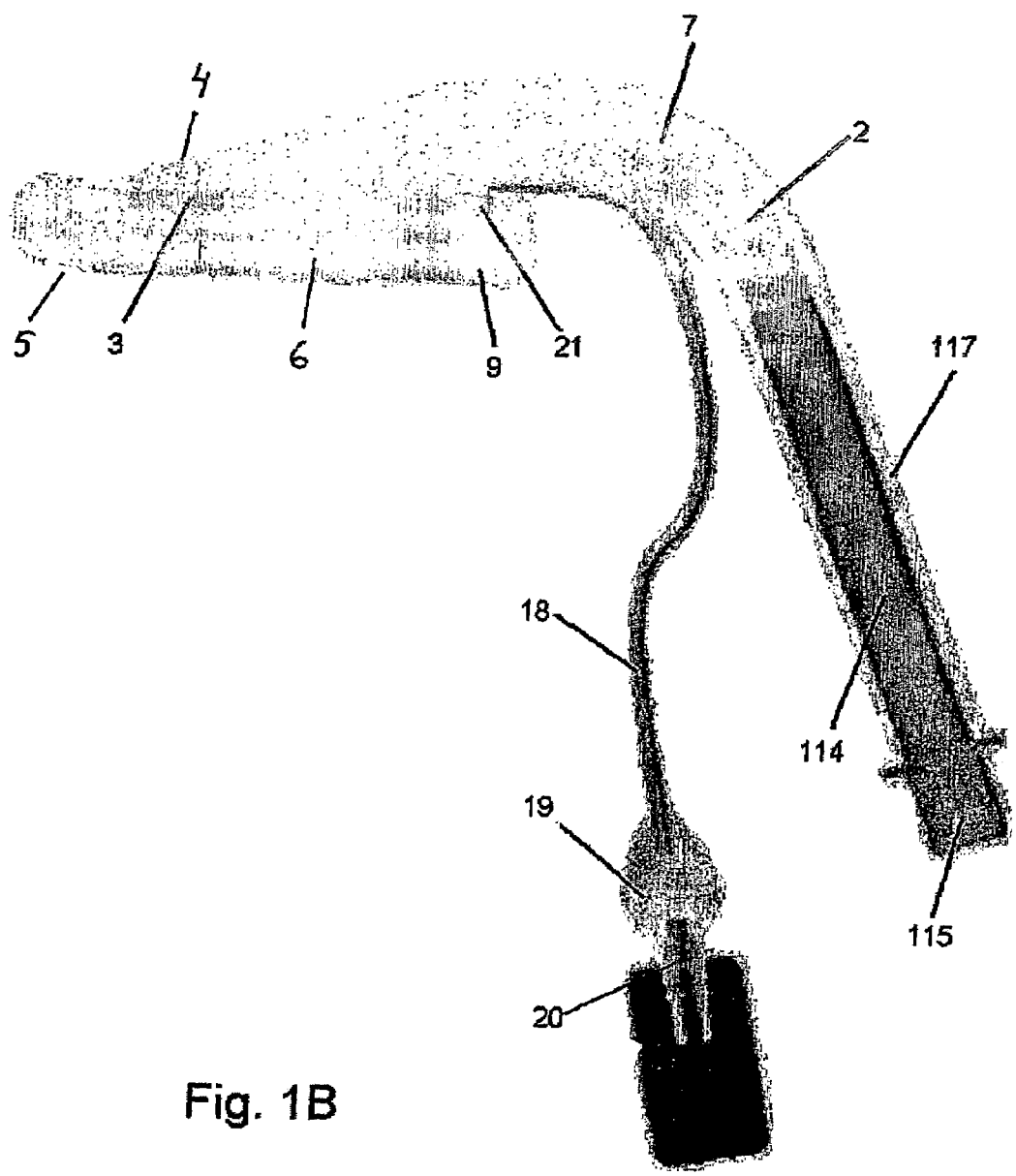

FIG. 1B distinguishes itself from the one shown in FIG. 1A in that it further comprises a rigid tubing 114 which is a straight piece of hollow piping manufactured from a plastics material, eg rigid PVC, albeit it may also be made of metal, and extending at its free end into a conical connector 115, which rigid tubing 114 and connector 115 may be moulded integrally. The part of the rigid tubing 114 that does not comprise the connector 115 is surrounded by an exterior jacket 117 that is constituted of and is shaped as an integral part of the airway tube 2. The airway tube 2 is curved, and its lumen 7 communicates with the lumen 114 of the rigid tubing. The rigid tubing 114 can be configured in a number of ways. For instance, it may be corrugated, and likewise there may be guides, threads and the like in response to the desired bendability of the tubing. In the shown example the tubing is smooth.

It is noted that, as a minimum, the airway tube 2 consists of a curved portion and a straight portion. The curved portion will always constitute an integral part of the laryngeal mask.

Figure 1C:
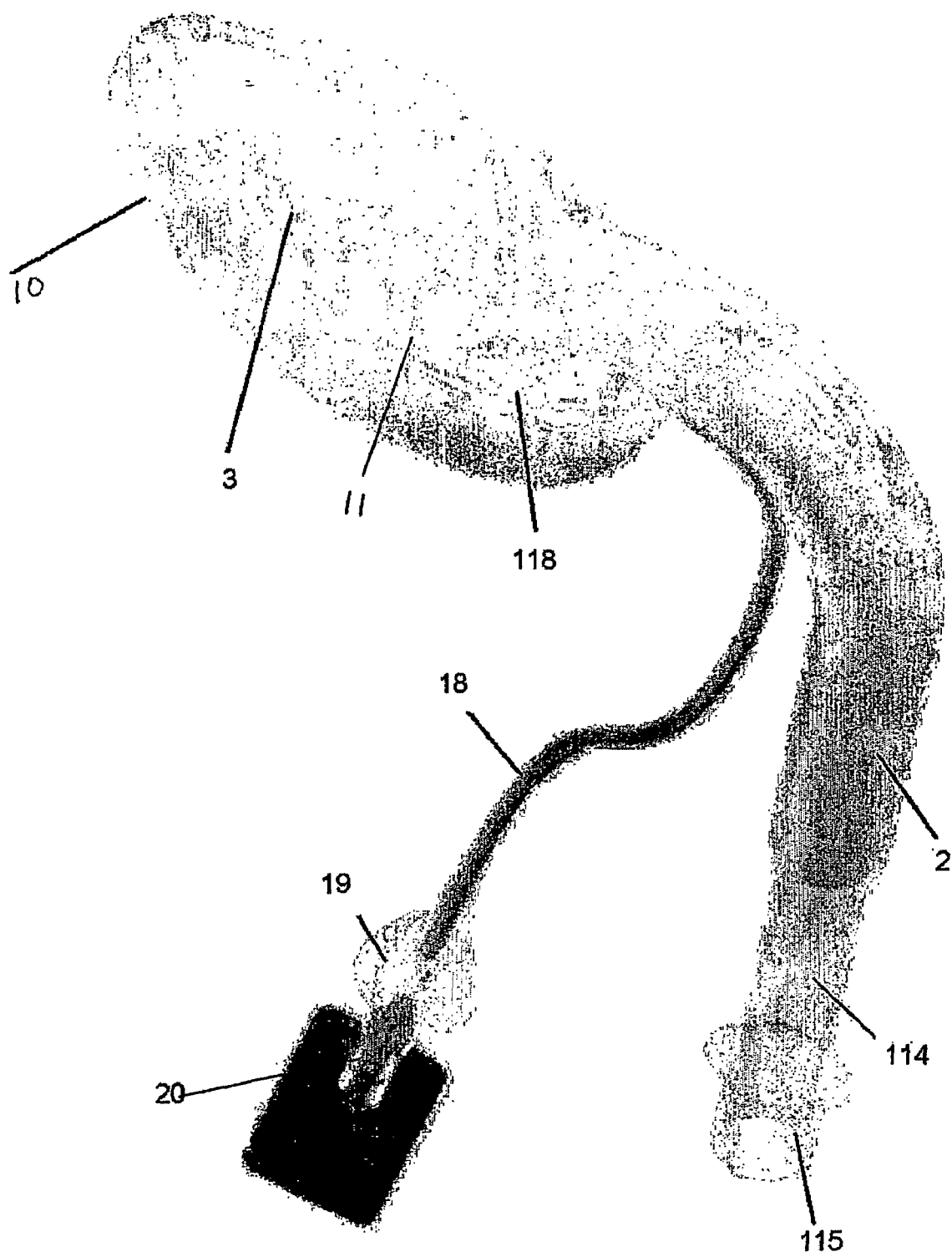
Figure 1D:
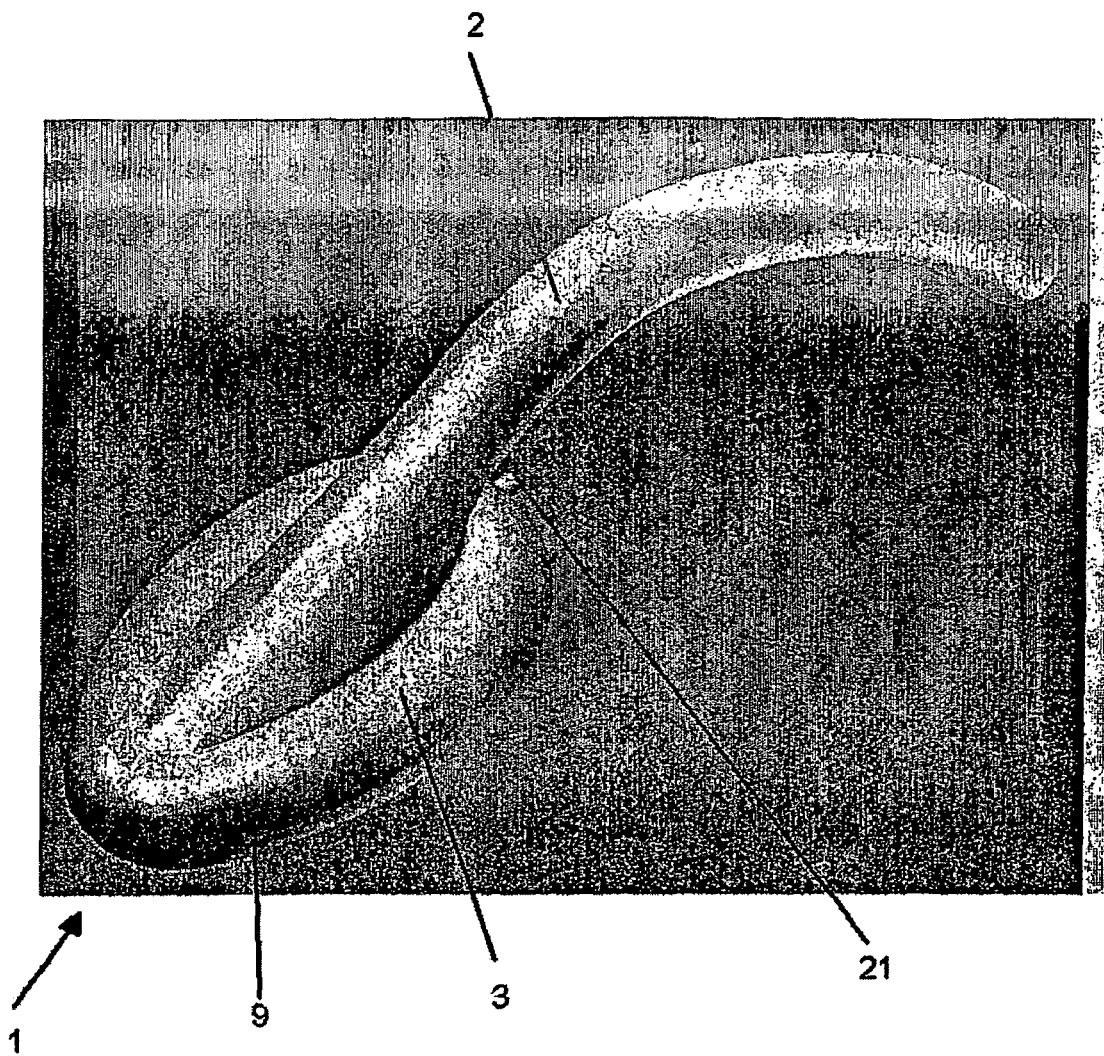

The laryngeal mask shown in FIG. 1C resembles essentially that of FIG. 1B; with the exception, however, that in this case the airway tube 2 is shortened and therefore it does not entirely enclose the rigid tubing 114. It is noted however, that the rigid tubing 114 may very well be configured such that it also comprises a curved portion that corresponds to the curved portion of the airway tubing 2. However, FIG. 1C shows that about half of the rigid tubing 114 is exposed. It is noted that the airway tubing 2 encloses the outer surface of the rigid tubing 114 so closely that it is not necessary to have assembly material between the outer surface of the rigid tubing 114 and the inner free face of the airway tube 2, although, conventionally, glue would be used between connector part and the airway tube as such. Moreover FIG. 1B, 1C and FIG. 1D show that the cuff 9 comprises a lower cuff portion 10 as well as an upper cuff portion 11, which upper cuff portion 11 is situated on the face 4 where the airway tube extends into the mask portion 3.

According to a preferred embodiment airway tube 2 and mask portion 3 are moulded around the rigid tubing 114 from a material that is able to adhere towards the material that was used for the rigid tubing 114. Thereby a very tight connection is accomplished, as the rigid tubing 114, the airway tube 2 and the mask portion 3 are thus in reality moulded integrally and are thereby caused to constitute one integral unit. In a preferred embodiment, the rigid tubing 114 is moulded from the same material as the airway passage 2.

FIGS. 2A-D show a first exemplary embodiment of the laryngeal mask and corresponds essentially the one shown in FIGS. 3A-C with the exception that the laryngeal mask 1 does not comprise an upper cuff portion 11. The exemplary embodiment shown in FIGS. 2A-D also essentially corresponds to the one shown in FIGS. 4A-D with the exception that this laryngeal mask does not comprise inflatable lateral bellows 12.

Thus, the sectional view shown in FIG. 2B differs from that of FIG. 3B ia in that the cuff 9 exclusively comprises a lower cuff portion 10 that extends around the entire peripheral circumference of the lumen 6 in an uninterrupted ring. In that depiction the laryngeal mask is shown in an intermediate stage, in which it is not yet fully assembled, an upper peripheral edge 14 and a lower peripheral edge 15 having to be assembled in order for the lower cuff portion 10 to constitute the closed annularly extending cuff 9. The lower cuff portion 10 is essentially symmetrical about its longitudinal axis, but asymmetrical about the short axis. The cuff portion 10 is thus generally elliptical as will be appreciated by study of FIG. 2C. Thus, the cuff 9, 10 do not extend to the upper face 4 of the embodiment shown in FIG. 2.

FIG. 3B is a sectional view along B-B in FIG. 3A, this further exemplary embodiment of a laryngeal mask comprising an annularly extending peripheral opening 13 in the inner periphery of the cuff 9, facing towards the lumen 6. The laryngeal mask is thus seen in an intermediate stage before the closed elliptical cuff 9 is produced. This opening is delimited by an upper peripheral edge 14 and a lower peripheral edge 15. Between those there is, prior to assembly of the cuff 9, a gap of between 1 and 8 mm. The closed inner periphery of the mask portion is produced by the upper 14 and the lower 15 peripheral edge, configured eg as a tongue 16 and groove 17 arrangement, also known as a male/female arrangement, are subsequently assembled adjoiningly, eg by a gluing process, for providing the closed airtight peripheral cuff 9. The two peripheral edges 14, 15 may have other shapes and may be assembled in other manners, eg by welding.

The airway tube 2 as such may comprise one or more sensory indicator beads 10 comprising bulges on the exterior face of the tube 2. They may optionally be arranged exclusively on a part of the airway tube and serve the purpose of facilitating arrangement of the laryngeal mask 1 by the operator. The sensory indicator bead 10 thus allows tactile determination of the position of the mask in the oral cavity during introduction of the mask 1. The sensory indicator bead 10 may of course also be used for the alternative embodiments of the laryngeal mask 1.

The mask portion 3 of the laryngeal mask may comprise an additional inflatable bellows or upper cuff portion 11 arranged on or constituting an integral part of the top face 4 of the mask portion. The bellows 11 may be provided by gluing of an additional piece of plastics film that is secured to the top face of the peripheral cuff, but it is preferably provided in the form of an enlarged portion of the cuff 9, whereby the cuff 9 consists of an upper 11 and a lower 10 cuff portion. Alternatively the bellows 11 can be configured in that, within the mask as such, an extra cavity is formed that is filled with air when the peripheral cuff 9 is inflated. The object of this is to ensure a closer abutment of the mask portion 3 around the laryngeal opening during use of the mask 1, the bellows 11 abutting on the wall of the pharynx opposite the laryngeal opening.

FIGS. 4A-D show a third exemplary embodiment of a laryngeal mask according to the invention and being essentially identical with the exemplary embodiment shown in FIG. 2, but wherein the peripheral cuff 9 of the mask portion 3 comprises at least two inflatable lateral bellows 12 that are arranged on the top face 4 of the mask and being essentially in parallel with the major axis of the generally elliptical cuff 9. Like above, it serves the purpose of ensuring a closer abutment of the mask portion 3 around the laryngeal opening during use of the mask 1, the lateral bellows 12 abutting on the wall of the pharynx opposite the laryngeal opening. Simultaneously passages (gullies) 4a are formed between the lateral bellows 12 and the upper face of the mask portion 3 that allow vomit, if any, to pass the mask portion. Thereby it is prevented that vomit, if any, displaces the mask portion 3 or parts thereof.

Besides, all of or parts of the mask 1 can be coated with a lubricant, thereby making it easier to arrange. Such agent is known from eg catheters and wherein the lubricant is activated eg by moistening. The coating adds hydrophilic properties to the product causing it to bind water upon moistening. An example of coating agen is PVP—polyvinylpyrrolidon—that also imparts antibacterial properties to the mask 1. Other coatings exclusively provide a hydrophilic surface.

Figure 6:
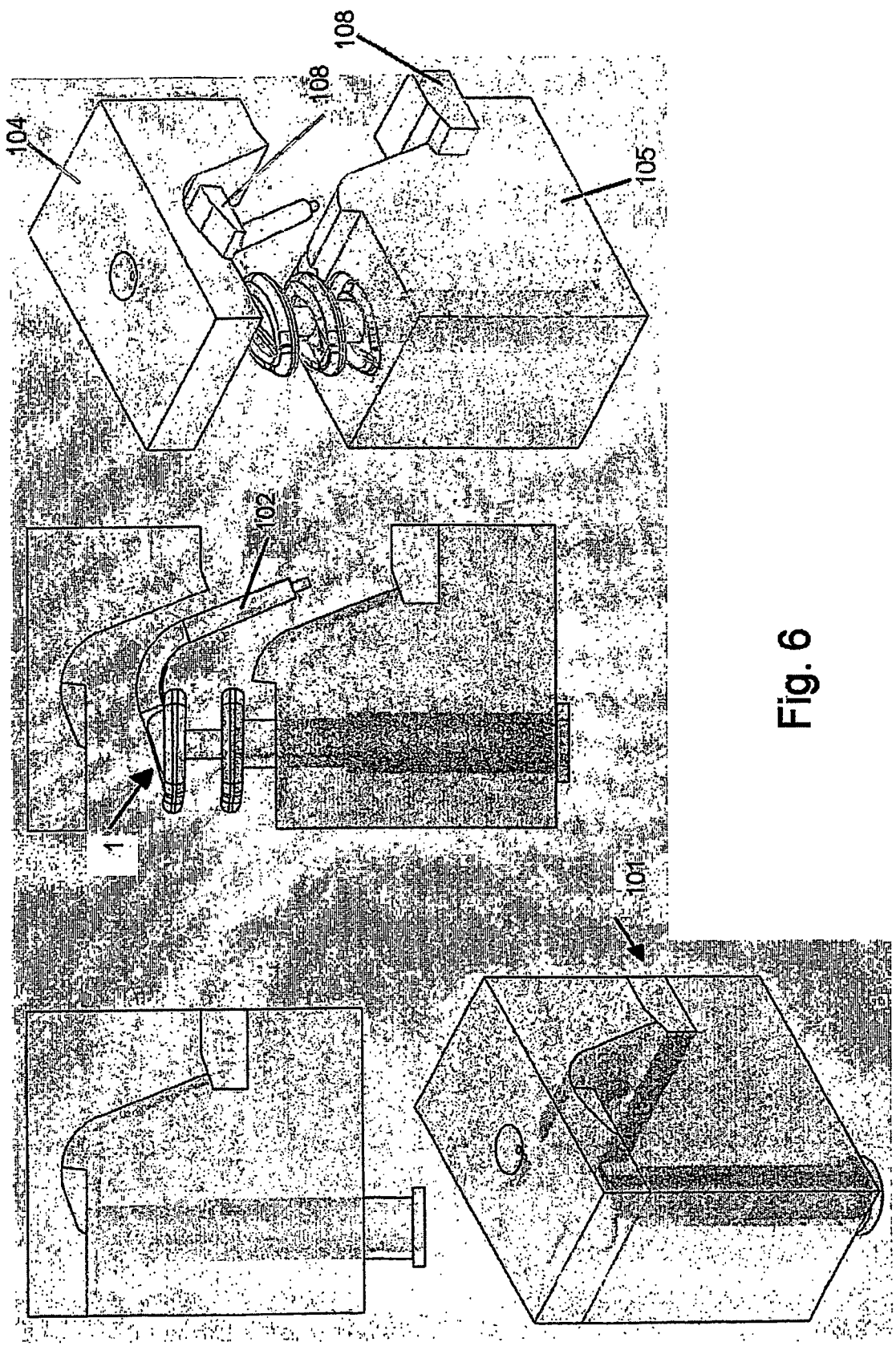
FIG. 6 shows a mould in a perspective view and as an x-ray photography.

The process of manufacturing the laryngeal mask 1 is shown in FIGS. 5-6 and takes place as an injection moulding process in a closed mould part 101, which laryngeal mask 1 comprises the airway tube portion 2 and the mask portion 3, and wherein the mask 1 is ejected from the mould after moulding. In an intermediate stage, the peripheral cuff 9 of the laryngeal mask 1 comprises an annularly extending opening 13 and is delimited by an upper peripheral edge 14 and a lower peripheral edge 15. The opening 13 faces towards the lumen 6 of the mask portion 3 and it ensures that it is possible to discharge the mask from the mould. The distance between the upper 14 and the lower 15 peripheral edge is 1-8 mm following discharge of the laryngeal mask 1 from the mould.

Liquid plastics material is injected into the closed mould 101 at a first pressure and a first temperature. The mould 101 comprises at least one core 102 that provides the interior lumen 7, 6 in tube 2 and mask 3 portions.

The mould 101 also comprises two first mould parts: an upper first mould part 104 and a lower first mould part 105, the interfaces 106 of which comprise a first interface 107 situated in the area corresponding to the lower face 5 of the mask. The two mould parts are movable perpendicular to each others interface 107. The interface in the area where the tube part is moulded coincides the area where its largest diameter is found.

The mould 101 also comprises two further second mould parts 108, whose other movement pattern is perpendicular to the movement line of the first mould part.

When the plastics material is injected into the mould 101 and the moulding of the laryngeal mask 1 is finished, it has to be removed. The lower first mould part 105 is moved away from the upper mould part 104, and the two second mould parts 108 are moved away from each other by use of the second movement pattern.

Subsequently the core 102 is moved in the same direction as the lower first mould part 105, and the laryngeal mask 1 is discharged from the mould. As mentioned previously, this is enabled by the annularly extending opening 13 provided in the peripheral cuff 9, the periphery of the mask portion 3 comprising an upper and lower 14 periphery configured eg with a tongue/groove arrangement 16, 17. To finish the laryngeal mask 1, they are assembled against each other, eg by a gluing process for providing an essentially closed peripheral cuff 9.

Besides, the core 102 may comprise two mutually movable core parts, wherein the one core part provides the cuff 9, while the other core part partakes in the provision of the remainder of the laryngeal mask 1.

The laryngeal mask 1 is subsequently provided with a tube 18 on the peripheral cuff 9, said tube 18 being at its free end provided with a valve 20 and a pilot balloon 19. This takes place in accordance with known principles and enables inflation of the peripheral cuff and ventilation thereof following use. The connector 115 can be manufactured along with the rigid tubing 114, or the connector 115 can be inserted on the free end (the distal one) of the airway tube 2 in accordance with known principles. It can be manufactured in a variety of colours as a function of the size of the laryngeal mask, and in this manner identification of the different sizes of laryngeal mask is made easier to the operator.

Figure 7:
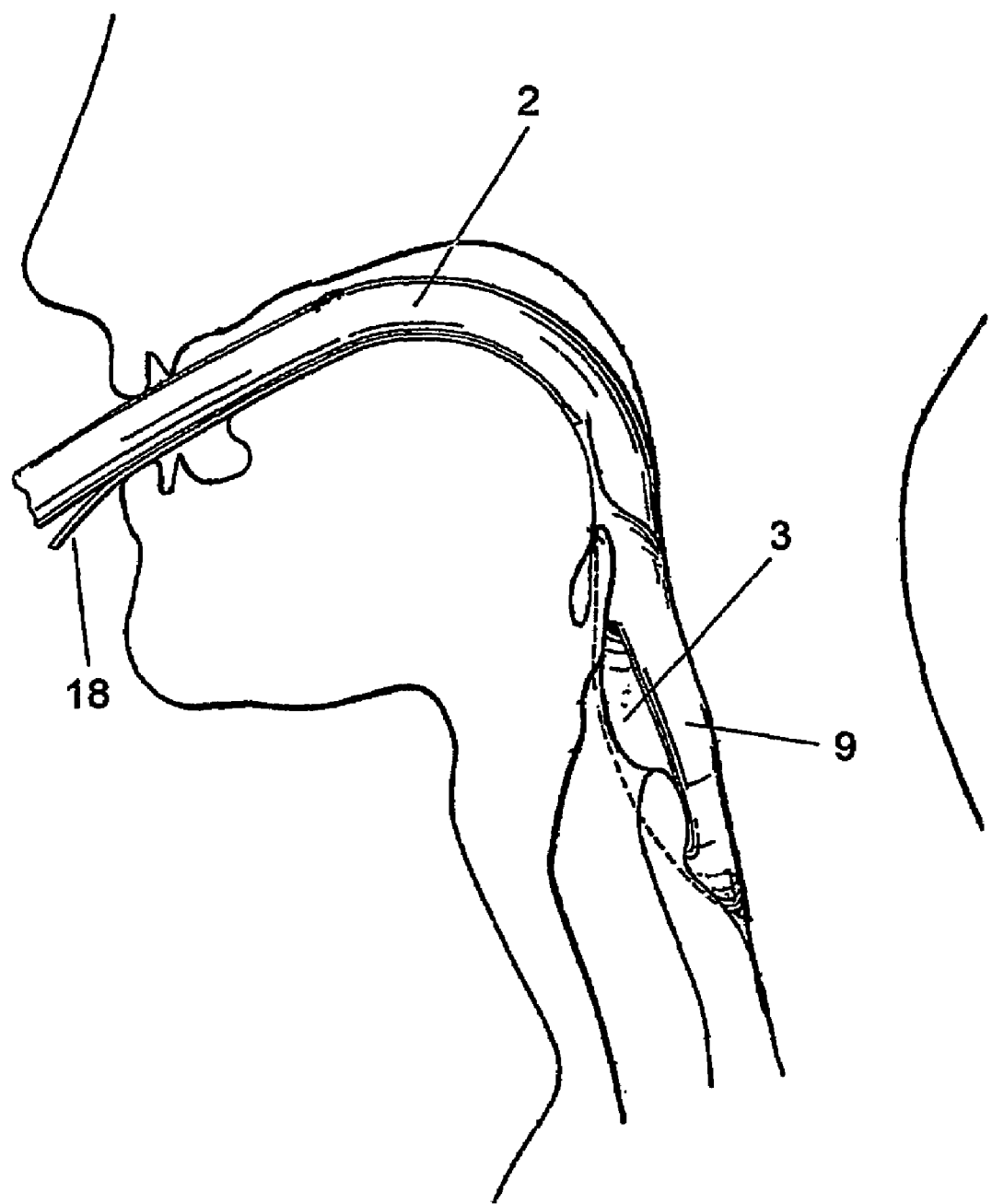
FIG. 7 shows a laryngeal mask according to the invention and arranged in situ.

FIG. 7 shows a laryngeal mask in situ. As will be appreciated by study of the Figure, the mask portion 3 is arranged for abutment around the laryngeal opening, the inflated cuff ensuring that abutment. The airway tube 2 extends through the pharynx and its free end can be connected eg to a respiratory apparatus. Likewise the second tube 18 is shown while extending through the pharynx. The second tube 18 is thus used for inflating the closed cuff 9.

Figure 8:
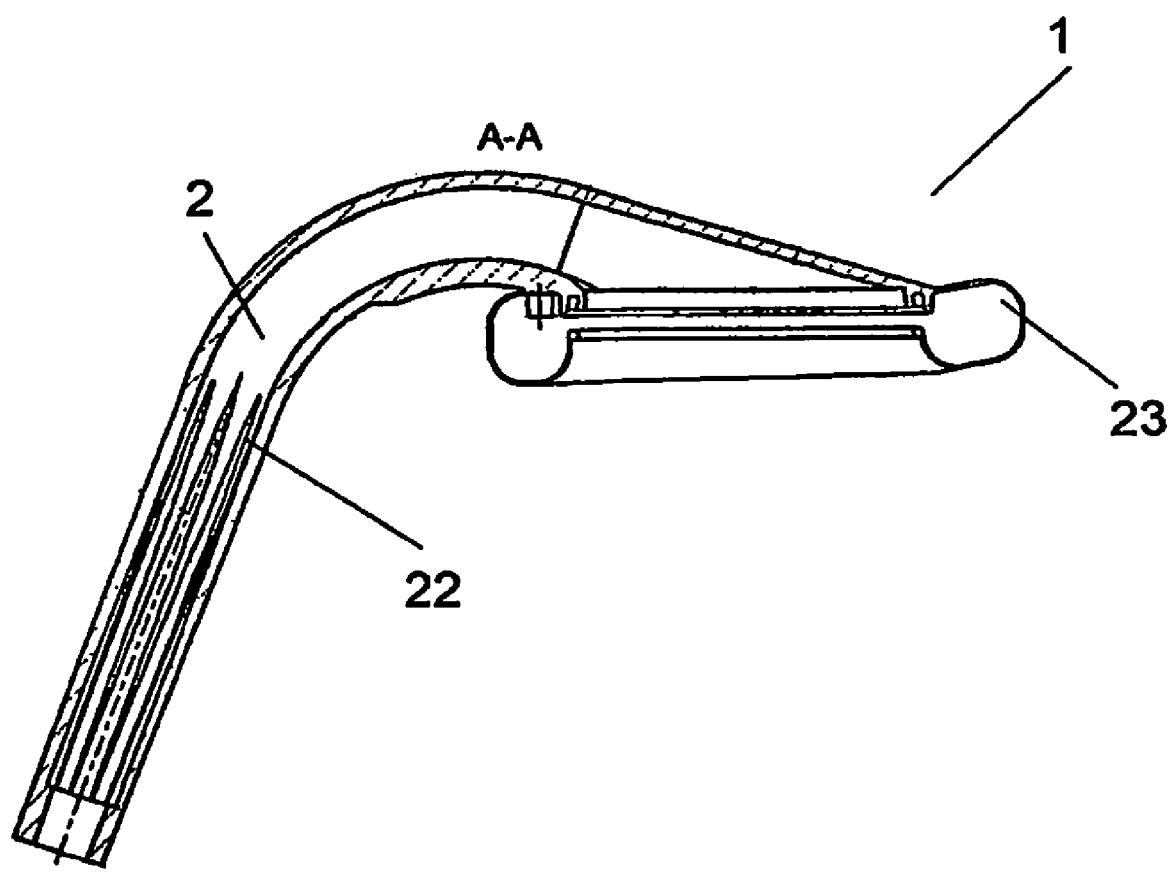
FIG. 8 shows a laryngeal mask according to the invention in a sectional view and comprising reinforcing ribs in the interior wall face of the air tube.

FIG. 8 shows an exemplary embodiment of a laryngeal mask 1 according to the invention and shown in a sectional view. It will appear from the Figure that, at its free, distal end, the airway tube 2 is provided with reinforcing ribs 22 that extend in parallel with the longitudinal axis of the airway tube 2 and are located on the face that faces towards the lumen 7. The ribs 22 will occur as a result of increased material thickness in sections of the airway tube 2.

These reinforcing ribs 22 impart increased rigidity in the area and contribute to preventing the tube 2 from kinking. Furthermore, in a section 23 of the mask portion 3—in particular the upper foremost end of the peripheral cuff 9—a thickening of the material thickness will appear to the effect that this fore thickness 23 exhibits increased rigidity compared to the cuff 9 in general. Thereby improved introduction of the product into the patient is ensured, as such rigidity prevents this section of the mask portion 3 from bending or folding during introduction of the laryngeal mask 1 into the pharynx of the patient.

The Figure also shows a pronounced curvature between mask portion 3 and the airway tube 2, the longitudinal axis of the airway tube 2 forming an angle to the longitudinal axis of the mask portion 3 of 60-90°.

In that context it should be noted that, as one of its distinctive advantages, the injection moulding enables regulation of the material thickness of the laryngeal mask 1 to the effect that portions or sections of the laryngeal mask 1 will exhibit smaller material thicknesses than other portions/sections.

Hereby it is possible to adjust the flexibility and rigidity of the laryngeal mask 1, and as was illustrated by the above-referenced constructive details in connection with the reinforcing ribs 22 and the fore thickening 23.

Likewise, small material thickness in an area that is exposed to pressure influences, ie typically the peripheral cuff 9, will balloon in these areas, ie be inflated to larger dimensions than the thicker areas and create bulges that will be visible only in connection with said inflation. Thus, the laryngeal mask 1 will appear with a uniform surface when not inflated. This property is utilized in connection with the additional inflatable bellows 11 and the inflatable lateral bellows 12 of the product.

Finally it is noted that the airway tube 2 may comprise a lining 114. It can be provided by performing a first moulding in a first plastics material of a first airway tube 114 and subsequently injecting a second plastics material into the closed mould and enclosing the outer faces of the first airway tube 114 and for providing an entire laryngeal mask 1 as described above. The first and the second plastics material need not bond to each other. This extra lining 114 in the airway tube 2 imparts other mechanical properties to the airway tube 2 in those sections than in the remaining sections of the airway tube 2 and in the laryngeal mask 1 as such, eg increased rigidity. As described above, this extra lining 114 may consist of a rigid tubing 114.

FIG. 9A is a sectional view along the median plane of the product shown in FIG. 1D, from where the wall thicknesses will appear. It this shown example the airway tube 2 has a wall thickness comprised within a second interval 112 and corresponding to 1.4-3 mm, preferably 1.5-3 mm, the wall thickness of the airway tube 2 varying within that interval c, d. The cuff 9 as such has a wall thickness comprised within a first interval 111 with a lower value a and an upper value b, said first interval 111 typically corresponding to 0.4-0.8 mm. In this context it is noted that those parts of the cuff 9 that are located in the immediate vicinity of and encircling the lumen 6 of the mask portion 3 will have a smaller thickness, while other portions/sections of the cuff 9, eg those corresponding to the upper wall 118 of the cuff 9, may very well have a larger wall thickness, it being in this case of less significance that the cuff 9 is capable of ballooning during inflation of the cuff 9. In the transition 4, 8 between cuff 9 and airway tube 2, the thickness will be within a third interval 113, preferably the interval ½-3 mm.

Figure 9:
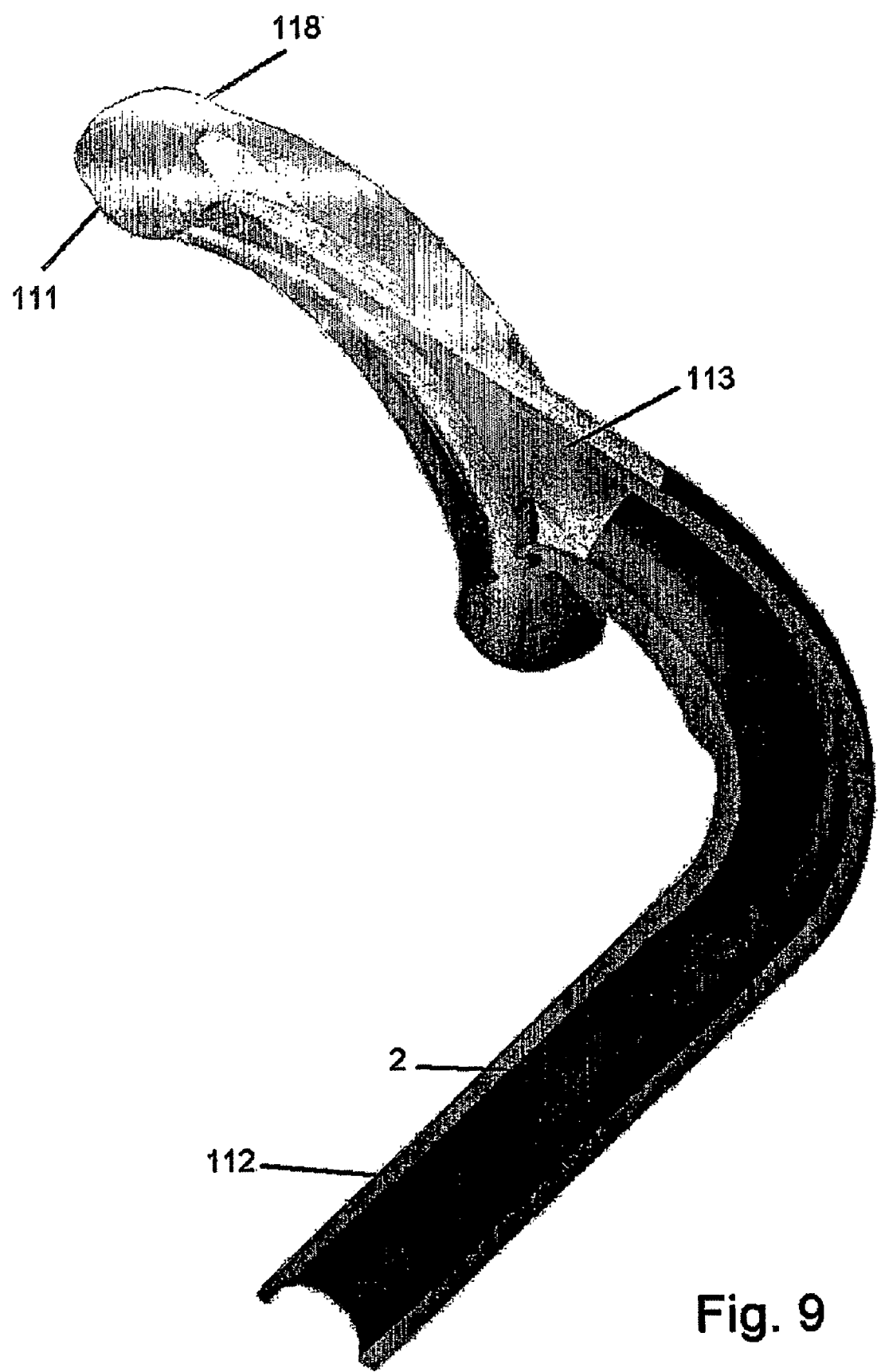
FIG. 9 is a sectional view along the median plane of the exemplary embodiment shown in FIG. 1D of a laryngeal mask and with indication of the thickness of the walls.
Figure 10:
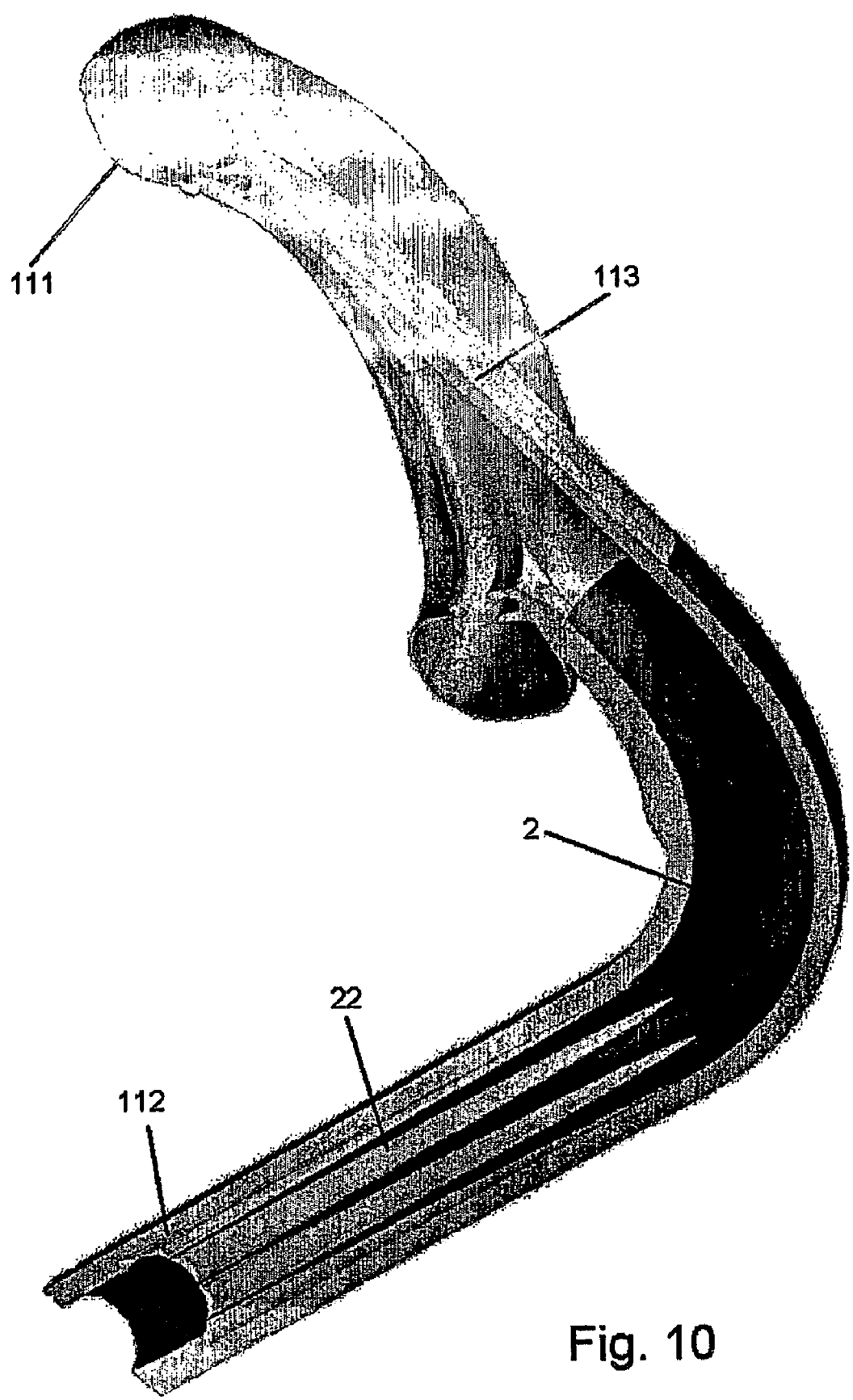
FIG. 10 is a sectional view along the median plane of the exemplary embodiment shown in FIG. 8 and indicating the material thicknesses of the walls.
Figure 11A:
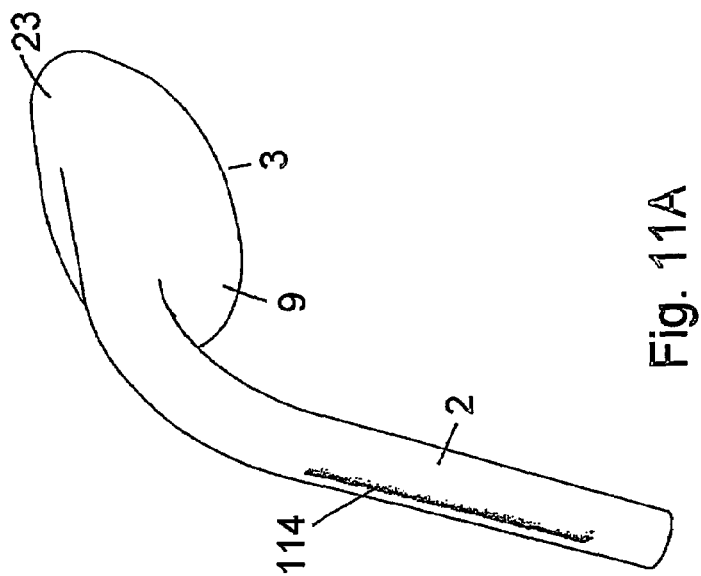
FIGS. 11A-C show material thicknesses of an exemplary embodiment of the laryngeal mask according to the invention, wherein Figure A shows the mask in a perspective view, Figure B the laryngeal mask seen from above, and Figure C the mask seen in section C-C from Figure B.
Figure 11C:
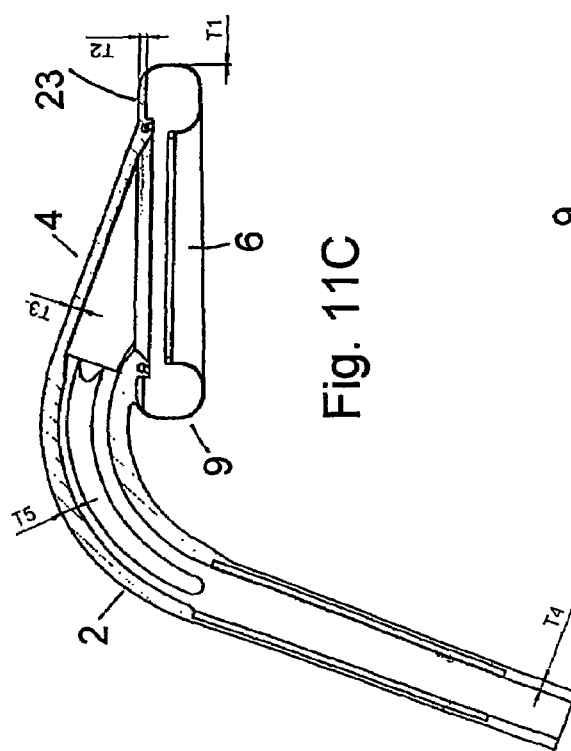
Figure 11B:
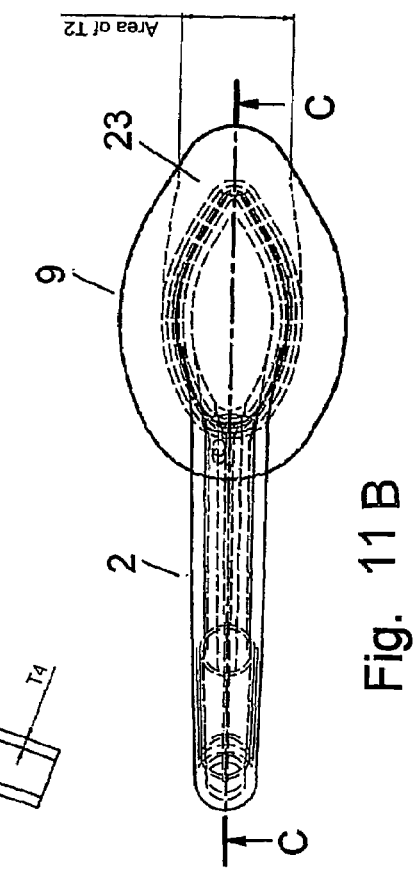

FIG. 10 shows essentially the same as FIG. 9, but wherein reinforcing ribs 22 are arranged in the airway tube 2 and extending from an upper area at a certain distance from the delimiting edge and corresponding essentially to the entire linear course of the airway tube 2, these reinforcing ribs 22 assuming a wall thickness of 2.5-3 mm and thus ensuring that the airway tube 2 does not kink, and likewise it enhances the mechanical properties of that part of the laryngeal mask 1.

The remaining parts of the walls of the laryngeal mask 1 have essentially the same dimensions as the one shown in FIG. 9. Besides, it is noted that the upper and lower values of the third interval 113 are such that the lower limit is larger than the a-value, and the upper limit is smaller than or equal to the d-value. Besides, in those cases when a lining/rigid tubing 114 is arranged within the laryngeal mask, the wall thickness will assume small dimensions in those sections 117 of the airway tube 2 that cover the lining/the rigid tubing. In that case, the airway tube 2 will typically be of a nature that mostly resembles a shroud that is positioned externally of the outer surface of the rigid tubing. In those cases, the thickness of the airway tube will be about 1.5 mm in those areas.

FIG. 12 shows an exemplary embodiment of a laryngeal mask according to the invention. The Figure shows the general wall thicknesses of different parts of a laryngeal mask 1. As will appear the cuff has another general wall thickness T1 comprised within said first interval 111, the airway tube 2 another general wall thickness T4 comprised within said second interval 112, while the transition 4, 8 has a general wall thickness T3 situated within the above third interval 113.

The term 'general wall thickness' as used herein is intended to designate that the wall thickness of the relevant part of the laryngeal mask 1 is essentially a specific wall thickness for the most sections of these parts, albeit sections of the relevant part may have a wall thickness which is not the general wall thickness.

As will appear from FIG. 12, this may concern eg a section 23 of the cuff 9 that has a wall thickness T2 which is larger than the remaining wall thickness T1 of the cuff. Such reinforcement, as described above, prevents the fore end of the cuff from kinking or folding during introduction of the laryngeal mask 1 into the pharynx of the patient. The general wall thickness 1 of the inflatable part of the cuff is preferably 0.4 mm, while the wall thickness T2 of the reinforced section 23 is preferably 1-2 mm depending on the size of the laryngeal mask.

FIG. 12 also shows that the curved part of the air tube 2 can be provided with ribs to increase the rigidity of that part of the tube 2. These ribs have a wall thickness T5 that exceeds the general wall thickness T4 of the airway tube 2. T5 is preferably 2.2-4.8, depending on the size of the laryngeal mask. Preferably the laryngeal mask is configured such that the general wall thickness T1 of the inflatable part of the cuff 9 than the general wall thickness T4 of the airway tube 2. The general wall thickness T3 of the transition section/top face 8, 4 is smaller than the general wall thickness T4 of the airway tube 2 and larger than the general wall thickness T1 of the inflatable part of the cuff 9.

It should further be mentioned that the airway tube may have areas that are transparent, whereby it is possible to see occurrences of water vapour on the airway tube interior, which indicates that respiration takes place. This may be provided in connection with the manufacturing process, wherein eg the core may be sanded to impart a rough surface thereto, but wherein the core is, in selected areas, completely smooth, meaning that the laryngeal mask 1 will be more transparent in the corresponding area on the mask 1. The rough surface on the core also means that the product is more readily ejected from the mould. These areas, where there is provided some kind of window in the airway tube is typically configured with a thickness of about 0.5 mm. That is a thickness that corresponds more or less to the wall thickness of the annular/elliptical inflatable cuff 9.

The rigid tubings 114 that do not exhibit any kind of flexibility may also be configured with windows in selected places that enable visual detection of any occurrences of water vapour.

Finally it should be noted that the laryngeal mask 1 as such can be configured in a variety of colours, or parts of the product can be provided with different colours such that it is readily apparent to the user which size of mask 1 is relevant in the actual situation, ie depending on which size the patient needs. Thus a yellow colour will correspond to one size for one patient, while a blue colour will correspond to another size. This will facilitate in particular the administrative task of the hospital sector and, likewise, it will ensure that errors will not occur in the handing-out procedure.

The invention also relates to a laryngeal mask 1' comprising at least one airway tube 2' and a mask portion 3', said mask portion 3' comprising a top face 4' and a bottom face 5', which bottom face 5' comprises a lumen 6' that communicates with the interior 7' of the airway tubing 2', and which top face 4' comprises a closed transition face 8', said mask portion 3' being at least on the periphery of the bottom face 5' delimited by an inflatable cuff 9', the cuff 9' of said mask portion 3' comprising inflatable means for abutment against a wall of a pharynx opposite a laryngeal opening for providing a tight connection of the mask portion and the laryngeal opening, and wherein passages are provided between these abutment means and the top face 4' of the mask portion.

These means comprise at least two inflatable lateral bellows 12' arranged on the top face of mask cuff 9' and being arranged essentially symmetrically about a longitudinal axis of the cuff (9').

The inflatable lateral bellows (12) are arranged on the top face (4) of the mask 1, are arranged essentially in parallel with the longitudinal axis of the cuff 9'.

FIG. 12 shows an exemplary embodiment of such laryngeal mask 1'.

Upon opening of the cuff 9', these lateral bellows 12' may press against the rear wall of the pharynx opposite the laryngeal opening and thereby increase the abutment pressure of the mask cuff 9' against the pharynx around the laryngeal opening. By a preferred configuration of the lateral bellows 12' it is thus obtained that the tightness of the mask 1 is, in case of pressure respiration of the patient, increased in case of high ventilation pressures, and simultaneously that free passages from the oesophagus are formed between the inflatable lateral bellows 12' across the top face 4' of the mask leading to the mouth cavity, as will be appreciated by comparison of FIG. 7 to FIG. 12. Thereby the laryngeal mask 1 allows that any vomit is able to pass the laryngeal mask 1', and it is ensured that such vomit does not penetrate between the laryngeal opening and the laryngeal mask 1, or displaces the laryngeal mask 1'. Thereby occlusion of the respiratory tracts of the patient is prevented.

Thus, compared to known laryngeal masks, the invention provides a laryngeal mask 1, 1' in a simple manner and featuring improved tightness in case of high ventilation pressures, and simultaneously a drain passage is provided for passage of stomach contents between the top face of the mask and the rear wall of the pharynx. The drain passage also allows insertion of a stomach tube for suction following introduction and inflation of the laryngeal mask 1, 1'.

The combination thus obtained of increased tightness in case of high ventilation pressures and provision of an open drain passage across the top face of the laryngeal mask makes a laryngeal mask 1, 1' according to the invention well suited for use with patients suffering from acute respiratory arrest, since both high ventilation pressures and vomiting of stomach contents are relevant when such patients are being treated.

As was described above, the lateral bellows can also be used for an integrally injection-moulded laryngeal mask 1 wherein the same advantages are achieved.

Prior art for accomplishing these properties individually by laryngeal masks is described in the following patents and applications that are all, however, associated with drawbacks compared to this invention: U.S. Pat. No. 5,355,879 and U.S. Pat. No. 5,871,012 describe masks with means for increasing the tightness of the mask in case of high ventilation pressures; U.S. Pat. No. 5,241,956 and U.S. Pat. No. 6,439,232 describe masks provided with drain tubing.

According to an embodiment of the invention, the lateral bellows 12' can, as shown in FIG. 13, be manufactured such that, prior to inflation, they are oriented in a direction into the inflatable cuff 9'. This will facilitate arrangement of the laryngeal mask 1'. When the cuff 9' is inflated, the lateral bellows will thus assume a shape as shown in FIG. 12.

LIST OF REFERENCE NUMERALS

Laryngeal mask: 1
Airway tube: 2
Mask portion: 3
Top face: 4
Bottom face: 5
Lumen: 6
Tube interior: 7
Closed face: 8
Elliptical cuff: 9
Indicator bead: 10
Additional inflatable bellows: 11
Two inflatable lateral bellows: 12
Annularly extending opening in elliptical cuff: 13
Upper peripheral edge: 14
Lower peripheral edge: 15
Tongue: 16
Groove: 17.
Tube: 18
Valve: 19
Pilot balloon: 20
Stud: 21
Reinforcing ribs: 22
Fore thickening: 23
Mould: 101
Core: 102
Upper first mould part: 104
Lower first mould part: 105
Interface: 106
First interface: 107
Second mould parts: 108
Edge delimitation: 110
$1^{st}$ interval: 111
$2^{nd}$ interval: 112
$3^{rd}$ interval: 113
Rigid tubing: 114

Connector: 115
Airway tube wall: 116
Outer jacket: 117

The invention claimed is:

1. A method of manufacturing a laryngeal mask comprising an airway tube having a lumen and a mask portion, said mask portion comprising an inflatable cuff and an intermediary portion forming a transition from said airway tube to said inflatable cuff, said process comprising injection moulding of the airway tube, the intermediary portion and a cuff having an annularly extending opening between a second peripheral edge of said cuff and said intermediary portion integrally in a closed mould part in a first step, the material thickness of the airway tube, the intermediary portion and the cuff being regulated by the closed mould part, ejecting the airway tube, the intermediary portion and the cuff having the annularly extending opening from the mould in a second step, and providing a closed inflatable cuff by closing of the annularly extending opening of the cuff by assembling the second peripheral edge of the cuff with said intermediary portion by a joint.

2. The method according to claim 1, wherein a distance between the second peripheral edge and the intermediary portion at the annularly extending opening is 1-8 mm.

3. The method according to claim 1, wherein liquid polymer material is injected into a closed mould at a first pressure and a first temperature, wherein the mould comprises at least one core for providing the inner cavity in tube and mask portions, wherein the mould also comprises two first mould parts, an upper first mould part and a lower first mould part, whose interfaces comprise a first interface that is situated in the area corresponding to a lower face of the mask and movable perpendicular to each other's interface; and wherein the mould also comprises two further second mould parts, whose second movement pattern is perpendicular to the movement line of the first mould part;

the lower first mould part is moved away from the upper mould part;

the two second mould parts are moved away from each other by use of second movement pattern;

the core is subsequently moved in the same direction as the lower first mould part; and the laryngeal mask is finished by ejection from the mould and closing of the annularly extending opening.

4. The method according to claim 3, wherein portions of the surface of the core is/are rough.

5. The method according to claim 1, wherein a periphery of the mask portion is formed by an upper and a lower periphery configured by a tongue/groove arrangement, also known as a male/female arrangement, that is subsequently assembled against each other for providing an essentially closed peripheral cuff.

6. The method according to claim 1, wherein a rigid tubing is arranged in extension of the airway tubing to the effect that an outer jacket configured as an integral part of the airway at least partially encloses the outer faces of the rigid tubing.

7. The method according to claim 6, wherein the airway tube and the mask portion are moulded around the rigid tubing.

8. The method according to claim 7, wherein the airway tube, the mask portion and the rigid tubing are manufactured from the same polymer material.

9. The method according to claim 1, wherein a tube is subsequently mounted on the peripheral cuff of the laryngeal mask, which tube is at the other end provided with a valve and pilot balloon.

10. A laryngeal mask comprising at least one airway tube and a mask portion, which mask portion comprises a top face and a bottom face, said bottom face comprising a lumen that communicates with the tube interior, and said top face comprising a closed transition face, said mask portion being at least on the bottom face in the periphery delimited by an inflatable cuff, wherein the cuff of the mask portion comprises at least two inflatable bellows that are arranged on a top face of the inflatable cuff and are symmetrical about a longitudinal axis of the cuff, said at least two inflatable bellows being provided for abutment against a wall of a pharynx opposite a laryngeal opening for providing a tight connection of the mask portion and the laryngeal opening; and respective gully formed between each of said at least two inflatable bellows and the top face of the mask portion.

* * * * *